(12) United States Patent
Fehrenbacher et al.

(10) Patent No.: US 8,384,054 B2
(45) Date of Patent: Feb. 26, 2013

(54) MULTIPLANAR IRRADIATION DEVICE WITH TREATMENT BEAM DIRECTED OPPOSITE AN ACCESS

(75) Inventors: Georg Fehrenbacher, Muehltal (DE); Torsten Radon, Ober-Moerlen (DE)

(73) Assignee: GSI Helmholtzzentrum fuer Schwerionenforschung GmbH (DE)

( * ) Notice: Subject to any disclaimer, the term of this patent is extended or adjusted under 35 U.S.C. 154(b) by 470 days.

(21) Appl. No.: 11/996,498

(22) PCT Filed: Jul. 20, 2006

(86) PCT No.: PCT/EP2006/007131
§ 371 (c)(1),
(2), (4) Date: Jan. 22, 2008

(87) PCT Pub. No.: WO2007/009786
PCT Pub. Date: Jan. 25, 2007

(65) Prior Publication Data
US 2008/0203323 A1      Aug. 28, 2008

(30) Foreign Application Priority Data
Jul. 22, 2005  (DE) .......................... 10 2005 035 141

(51) Int. Cl.
*G21F 7/00* (2006.01)
(52) U.S. Cl. ............... 250/515.1; 250/505.1; 250/517.1; 250/518.1; 600/1
(58) Field of Classification Search ............... 250/492.1, 250/505.1, 515.1, 517.1, 518.1; 600/1–2
See application file for complete search history.

(56) References Cited

U.S. PATENT DOCUMENTS

| 4,139,777 A | * | 2/1979 | Rautenbach | 376/112 |
| 5,161,546 A | * | 11/1992 | Bronn | 128/897 |

(Continued)

FOREIGN PATENT DOCUMENTS

| DE | 100 10 523 A1 | 9/2001 |
| DE | 102 35 116 A1 | 2/2004 |

(Continued)

OTHER PUBLICATIONS

D.J. Dawson, LRCP Doorless Entry System, Medical Physics, Feb. 1998, vol. 25, No. 2, American Association of Physicists in Medicine, Department of Physics, London Regional Cancer Centre, Cancer Care Ontario, 790 Commissioners Rd. E., London, Ontario, Canada, N6A 4L6.*

(Continued)

*Primary Examiner* — Phillip A Johnston
*Assistant Examiner* — Brooke Purinton
(74) *Attorney, Agent, or Firm* — Kaplan Breyer Schwarz & Ottesen, LLP (57) ABSTRACT

Irradiation device for proton and/or ion beam therapy, said device comprising a radiation source, a beam guiding device, and a therapy room comprising a treatment site and an access, wherein the therapy room is arranged in a first plane, and the treatment beam is directed into the therapy room from a second plane above or below the first plane, and oriented towards the treatment site so that the treatment beam is directed away from the access. In the therapy room, a shielding is provided, which is open towards the treatment site and associated with the entrance region of the treatment beam into the therapy room so that the access is arranged on the side of the shielding opposing the treatment site, and a labyrinth leading from the access to the treatment site is provided laterally offset to the treatment beam proceeding in the therapy room and to the shielding.

20 Claims, 5 Drawing Sheets

U.S. PATENT DOCUMENTS

| | | | |
|---|---|---|---|
| 5,349,198 A * | 9/1994 | Takanaka | 250/492.3 |
| 5,433,693 A * | 7/1995 | Ott | 600/1 |
| 5,851,182 A * | 12/1998 | Sahadevan | 600/407 |
| 5,895,926 A * | 4/1999 | Britton et al. | 250/492.3 |
| 6,617,852 B1 * | 9/2003 | Danby et al. | 324/318 |
| 6,822,247 B2 * | 11/2004 | Sasaki | 250/492.21 |
| 7,030,398 B2 * | 4/2006 | Tajima | 250/505.1 |
| 7,397,044 B2 * | 7/2008 | Calderon et al. | 250/492.1 |
| 7,432,516 B2 * | 10/2008 | Peggs et al. | 250/492.3 |
| 2001/0027260 A1 * | 10/2001 | Uematsu et al. | 600/1 |
| 2002/0166293 A1 * | 11/2002 | Zeik et al. | 52/79.1 |
| 2004/0034301 A1 * | 2/2004 | Falco | 600/427 |
| 2004/0111134 A1 * | 6/2004 | Muramatsu et al. | 607/88 |
| 2004/0162457 A1 * | 8/2004 | Maggiore et al. | 600/1 |
| 2004/0223870 A1 * | 11/2004 | Herer et al. | 250/455.11 |
| 2005/0087700 A1 * | 4/2005 | Tadokoro et al. | 250/492.21 |
| 2005/0218348 A1 * | 10/2005 | Fehrenbacher et al. | 250/517.1 |
| 2007/0131876 A1 * | 6/2007 | Brahme | 250/492.1 |
| 2008/0308754 A1 * | 12/2008 | Fehrenbacher et al. | 250/517.1 |

FOREIGN PATENT DOCUMENTS

| | | | |
|---|---|---|---|
| DE | 10 2004 029 026 A1 | 12/2005 | |
| EP | 1 430 932 A1 | 6/2004 | |
| FR | 2821263 A1 * | 2/2001 | |
| JP | 02025798 A * | 1/1990 | |
| JP | 11176599 A * | 7/1999 | |
| JP | 2003528659 A | 9/2003 | |
| JP | 2011137372 A | 7/2011 | |
| NL | 1 009 865 C2 | 2/2000 | |
| WO | WO 2005053794 A1 * | 6/2005 | |

OTHER PUBLICATIONS

Mudahar et al. "Soil: A Radiation Shielding Material" Int. Journal of Radiation Applications and Instrumentation, Part A. vol. 39, Issue 1. 1988. pp. 21-24, abstract.*

G. Kraft, et al. "The Darmstadt Program HITAG: heavy ion therapy at GSI"; Hadrontherapy in Oncology: Proceedings of the International Symposium on Hadrontherapy, 1994, Darmstadt, Germany, XP-000949119.

Agosteo, S. et al.; "Shielding calculations for a 250 MeV hospital-based proton accelerator"; Nuclear Instruments & Methods in Physics Research, Section—A: Accelerators, Spectrometers, Detectors and Associated Equipment, May 21, 1996, Elsevier, Amsterdam, NL, XP-004007541.

Takeyama, Atsushi, "JP Application No. 2008-521890 Office Action Dec. 5, 2011",, Publisher: JPO, Published in: JP.

* cited by examiner

Fig.9

MULTIPLANAR IRRADIATION DEVICE WITH TREATMENT BEAM DIRECTED OPPOSITE AN ACCESS

BACKGROUND OF THE INVENTION

The invention relates to an irradiation device for proton and/or ion beam therapy according to claim 1. Such devices are known and are referred to as therapy facilities. Normally, they have a radiation source, which is implemented on base of a cyclotron or a synchrotron, with a beam guiding device as well as at least one therapy room, into which a treatment beam is directed. This beam is guided towards a treatment site, at which a patient to be treated may be placed.

When accelerating beams and using them in patient treatment, secondary radiation is generated. In the energy range to be considered herein of up to some 100 MeV per nucleon, neutrons, protons, light ions and gamma radiation are generated in nuclear reactions (spallation reactions or fragmentations of projectile or target nuclei), when decelerating ions. Shielding the secondary radiation is primarily dominated by the generated neutron radiation.

It is known that the largest part of an accelerated treatment beam is deposited in the tissue and generates there an highly forward-oriented—as seen in the direction of the treatment beam—cone of neutron radiation. Most of the generated neutrons exit the patient without interaction. Since the neutron radiation may have very high energies and the tenth value layer thickness equals one meter in standard concrete for example, particularly in the forward-direction of the incoming treatment beam, a substantial shielding effort is necessary. The constructional radiation protection design has to allow for those radiation-physical and geometric basic conditions.

When planning treatment centres, especially clinical facilities for particle therapy, in which irradiation devices of the type addressed herein are used, often the problem arises that this facility has to be built in an existing infrastructure close to or inside of a larger treatment centre. Due to the complex accelerator technology and the associated beam guiding devices, particle therapy facilities with cyclotrons and synchrotrons have a large floor space required. For providing treatment beams, a branched system of beam guidings is often needed in order to direct the beams of the radiation source into therapy rooms. Thus, the access to these rooms is often limited. Often, it cannot be avoided that the access to a therapy room is arranged in the region of the neutron radiation so that often heavy shielding doors have to be installed, which on the one hand increase the space required, and on the other hand, delay the access to the patient.

SUMMARY OF THE INVENTION

Therefore, it is an object of the invention to provide an irradiation device, which avoids the disadvantages stated herein.

For solving this object, an irradiation device for proton and or ion beam therapy with a radiation source, having the features stated in claim 1 is proposed. It comprises a beam guiding device and at least one treatment site and a therapy room with an access, into which therapy room a treatment beam for treating a patient is directed. The irradiation device is characterized by several planes being provided.

Thereby, the therapy room is arranged in a first plane. The treatment beam is directed from a second plane located above or below this plane into the therapy room and is directed towards the treatment site so that the treatment beam is directed away from the access. The space required can be reduced considerably, because parts of the irradiation device are arranged on different planes. Furthermore, the beam guiding device can be displaced out of the plane, in which the therapy room is arranged. Therewith, the access to the therapy room can be chosen independently of the beam guiding. With the irradiation device according to the invention it is provided that in the therapy room, there is provided a shielding being open to the treatment site. The shielding protects the further regions of the therapy room against the radiation. The access to the therapy room is arranged on the side of the shielding which faces away the treatment site so that at least one labyrinth leading from the access to the treatment site can be provided laterally offset in relation to the treatment beam proceeding in the therapy room and to the shielding. This labyrinth is not hit by the treatment beam. The neutron radiation, which may be generated downstream of the treatment site, does not hit the labyrinth, too. Therefore, the access to the therapy room can be protected against reflected radiation by the labyrinth solely, particularly, heavy shielding doors can be omitted. Therewith, an easy and fast access to the treatment site results.

The shielding effort can be reduced, because the neutron radiation generated in the therapy room in the region of the treatment site just does not hit the access and the labyrinth between the access and the treatment site, as it is the case with the therapy room according to DE 102 35 116 A1. This decreases the space required by the irradiation device.

With a preferred embodiment of the irradiation device, it is provided that a labyrinth is provided between the access and the treatment site on both sides of the shielding. One of the two can be used as access, and the other one as exit, so that using the therapy room can be optimized: The removal of patients does not hinder the access so that exchanging the patients is possible quickly.

A further preferred embodiment of the irradiation device is characterized in that rooms serving for the pre-treatment and for the after-treatment of patients and for the stay of further persons respectively may also be arranged on the first plane, in which the therapy room is located. This enables an optimization of the course of the therapy preparation (computer tomography, x-raying for verification of position etc.) and of the therapy procedure.

A further embodiment of the irradiation device is characterized in that the treatment beam entering the therapy room is directed towards the treatment site but not towards the rooms mentioned. Therefore, these rooms are in any case not be contaminated by the treatment beam and by the neutron radiation generated during treatment. Thereby, a special shielding between the entrance region and the mentioned rooms is not even necessary, because the therapy room may be arranged in such a manner that the neutron is directed into the soil for example, where a contamination of patients, treatment staff and persons, who operate and maintain the irradiation device is avoided.

With a further preferred embodiment of the irradiation device, it is provided that the radiation source is arranged in a third plane. The individual elements like radiation source, beam guiding device and therapy rooms may quasi be nested one upon the other to minimize the space required, because the irradiation device is distributed over several planes and because a further plane is opened here. Though, it remains provided that the beam directed towards the treatment site is directed away from the rooms, in which patients and further persons may stay.

Further embodiments result from the remaining subordinate claims.

BRIEF DESCRIPTION OF THE DRAWINGS

In the following, the invention will be explained in more detail by means of a drawing. It is shown.

DETAILED DESCRIPTION OF THE INVENTION

Figure 1:
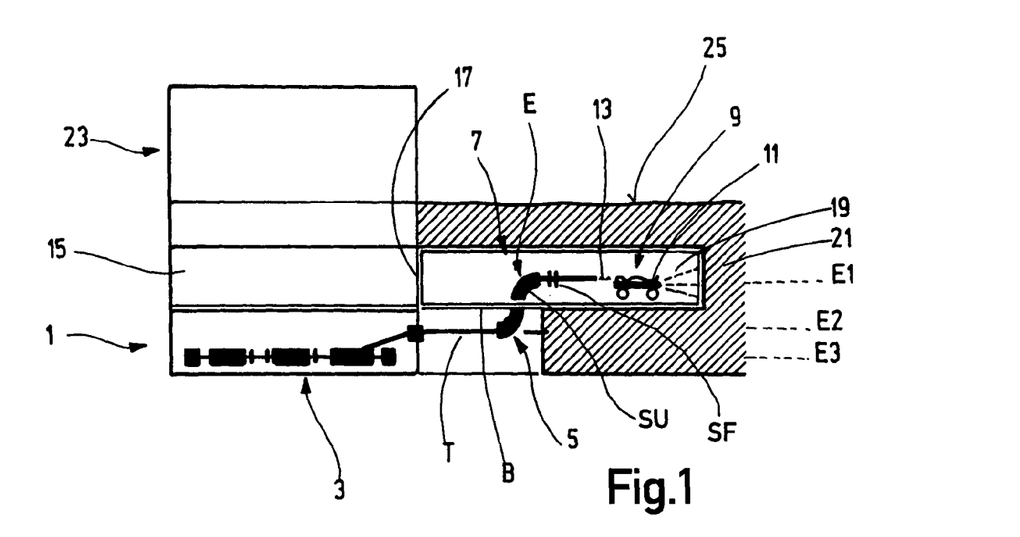
FIG. 1 a schematic diagram of an irradiation device in longitudinal section.

The schematic diagram according to FIG. 1 shows an irradiation device 1, which comprises a radiation source 3, beam guiding device 5 and a therapy room 7 with a treatment site 9, at which a patient can be exposed to a treatment beam 13. The schematic diagram shows that the therapy room is located on a first plane E1, while the beam guiding device 5 is arranged on an second plane E2 and the radiation source 3 is arranged on a third plane E3, wherein here the planes E2 and E3 are arranged below the first plane E1. But it is very well imaginable that the beam guiding device 5 and the therapy room 7 are arranged below the radiation source 3.

From the schematic diagram according to FIG. 1 it is apparent that the beam exiting the beam guiding device 5 enters the therapy room 7 in an entrance region E.

FIG. 1 shows further that a beam deflecting device SU as well as a beam forming device SF are provided in the therapy room 7 above the beam guiding device 5.

Next to the therapy room 7 a room 15 is indicated, which may serve the preparation of patients and in which operating staff for the irradiation device may stay.

The illustration shows that the radiation source 3, the beam guiding device 5 and the therapy room 7 as well as further rooms associated with the irradiation device 1, here room 15, may be arranged on top of each other, which results in a considerable saving of space. Moreover it appears that here the beam guiding device 5 is arranged below the therapy room 7 and thus does not disturb the access to the therapy room 7. With the irradiation device according to FIG. 1 it is provided that the access 17 is located in the transit region between the room 15 and the therapy room 7. In the illustration according to FIG. 1 one therefore enters the therapy room 7 from room 15 by going from left to right through the access 17. In the illustration according to FIG. 1, one accordingly reaches from therapy room 7 from right to left into the room 15. The entrance region E is located inside the therapy room 7 in a distance to the right of the access 17 and in a distance in the left of the treatment site 9.

In no case the access 17 is affected by the treatment beam 13, because the treatment beam 13 starting at the entrance region E passes through the therapy room 7 from left to right, Also, neutron radiation given beyond the treatment site 9 hits the access 17 in no case. As seen from the entrance region E, it proceeds to the right and is rather guided into the soil following the therapy room 7, the soil which is also provided above the therapy room 7. Therefore, it will become apparent that—seen in the direction of the treatment beam 13—no special shielding has to be provided beyond the treatment site 9, because, as mentioned, the neutron radiation 19 is guided into the soil 21 and therefore might not reach the room 15 in no case, which—seen in the direction of the treatment beam 13—is arranged at the side of the therapy room 7 opposite to the treatment site 9.

Also, the figure shows clearly that the access 17 is stressed neither by the treatment beam 7 nor by the neutron radiation 19.

The lateral view shows that the beam guiding device 5 is constructed such that a partial beam T of the radiation source 3 is directed into the therapy room 7 in the entrance region E from below through the floor of the therapy room 7 and is there deflected in such a manner that it proceeds parallel to the floor B, thus horizontally towards the treatment site 9.

Deflecting the partial beam T may also be chosen in such a manner that it enters the therapy room 7 in an angle, or in such a manner, however, that it is deflected inside the therapy room 7 in such a way that it does not proceed parallel to the floor B, but in angle to the floor. Therewith, the treatment beam 13 proceeds in an angle to the floor B in the treatment site 9 also.

Therefore, it is apparent that the irradiation device 1 may variably be designed concerning this aspect also. Thereby, it is also possible that the treatment beam 13 enters the therapy room 7 in an angle through the ceiling of the therapy room 7 or that there it is deflected in such a manner that it hits the treatment site 9 not parallel to the floor B, but transversely from above. This radiation path has the advantage that the treatment beam 13 and the neutron radiation 19 are guided into the soil 21 from above so that an optimal absorption is ensured. With a radiation path transversely upwards, it would have to be ensured that the soil 21 above the therapy room 7 is thick enough or that a shielding is there provided additionally.

In some cases, a gantry can be set aside, because here it is made possible to direct the partial beam T and particularly the treatment beam 13 onto the treatment site 9 in an angle.

The illustration also shows that the entrance region E into the therapy room 7 of the partial beam T is located in a distance to access 17 into the therapy room 7 and in a distance to the treatment site 9. Thereby, it becomes particularly apparent that region between the access 17 and the entrance region E is free, because here the beam guiding device 5 is arranged below the floor B.

In FIG. 1, it is indicated that the room 15 may be part of a treatment centre, a research centre or a hospital 23.

Also above the therapy room 7, there is soil 21. By the arrangement below the ground level 25, the shielding by concrete and other materials may be reduced to a minimum above the therapy room 7 also.

Overall, voluminous shielding masses may be avoided inside the irradiation device 1 and the hospital 23, because natural shielding materials, namely soil 21, may be used, which additionally brings down costs of installation, but of deconstruction also.

Overall, the following advantages result:

By arranging the elements of the irradiation device 1 on different planes E1, E2, and E3 it is particularly possible to provide the beam guiding device 5 in another plane than the therapy room 7 so that the access 17 to this room and the rooms 15, which are necessary in conjunction with using the therapy room 7, may be optimally arranged and that the course of therapy preparation and of therapy procedure is undisturbed. Furthermore, the constructional radiation protection for the radiation source 3, the beam guiding device 5 and for the therapy room 7 is guaranteed. Shielding materials are used very efficiently. Particularly, expensive materials like concrete and the like may be substituted by soil. Furthermore, the individual elements of the irradiation device 1 may be arranged compactly and the space usage may be optimized. Incidentally, the linking to existing treatment or research centres, particularly to hospitals, is possible without additional radiation exposure by treatment beams or neutron radiation arising there.

Figure 2:
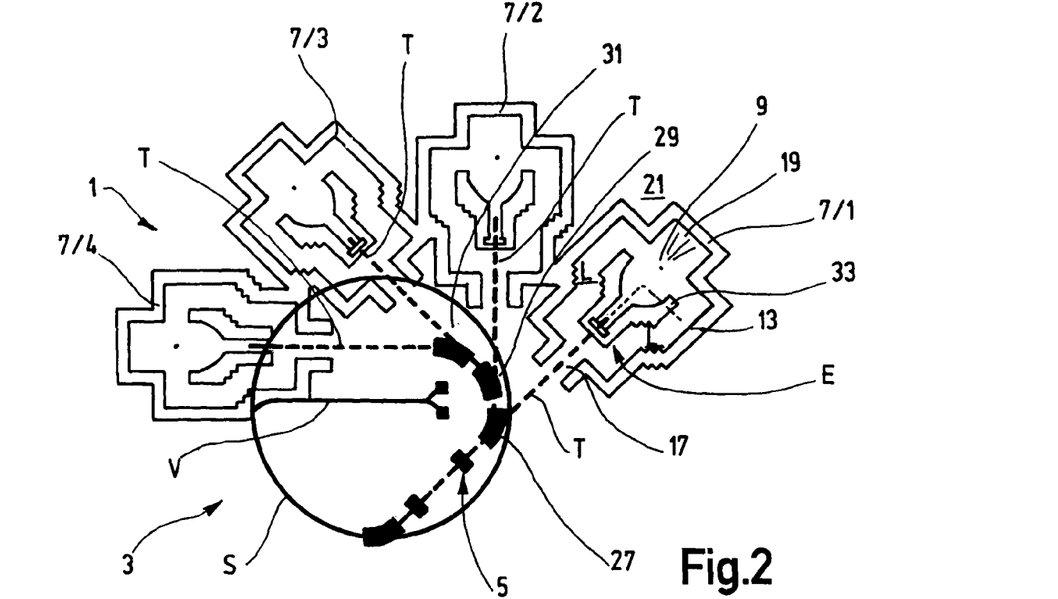
FIG. 2 a top view of the irradiation device shown in FIG. 2.

In top view, FIG. 2 shows the irradiation device 1 depicted in FIG. 1. Here, the radiation source 3 may clearly be seen, which comprises a pre-accelerator V, also referred to as LINAC, and a synchrotron S. The radiation source 3 is located in the lowest plane E3.

Above this plane, the beam guiding device 5 with several beam branchings 27, 29 and 31 is located in the plane E2. Above the plane E2, here there are four indicated therapy rooms 7/1, 7/2, 7/3, and 7/4.

From the illustration according to FIG. 2, it becomes apparent that, seen from the radiation source 3, beyond the beam branchings 27, 29, and 31, partial beams T are given, which are fed into the therapy rooms 7/1 to 7/4.

Because here the therapy rooms are identically constructed, only the therapy room 7 will be described in the following. The further explanations will be given by means of the therapy room 7/1 rightmost depicted in FIG. 2; in the following, this room will generally be referred to as therapy room 7.

The access 17 to the therapy room 7 is oriented in such a manner that it points in the direction of the partial beam T, wherein it will be apparent from the comments on FIG. 1 that the partial beam T proceeds below the floor B of a therapy room 7 and in the first place enters—here from below—the therapy room 7. It is self-explanatory that such a beam leading-in may also occur from above.

In the illustration according to FIG. 2, the isocentre at the treatment site 9 is indicated by a point. The treatment beam 13 entering the therapy room 7 in the entrance region E is directed towards this isocentre. Neutron radiation given beyond the treatment site 9 is directed away the access 17 and enters the soil 21 surrounding the therapy room 7. Here, it becomes apparent also that the access 17 is stressed neither by the treatment beam 13 nor by the neutron radiation 19.

The entrance region E is surrounded by a quasi U-shaped shielding 33 being open towards the treatment site 9. As seen from the access 17 towards the treatment site 9, there is at least one labyrinth L beside the shielding 33. With the embodiment depicted in FIG. 2, a labyrinth is provided each to the right and to the left of the shielding 33. One of those labyrinths may be used as access, the other as exit, in order to optimize the therapy procedure.

Figure 3:
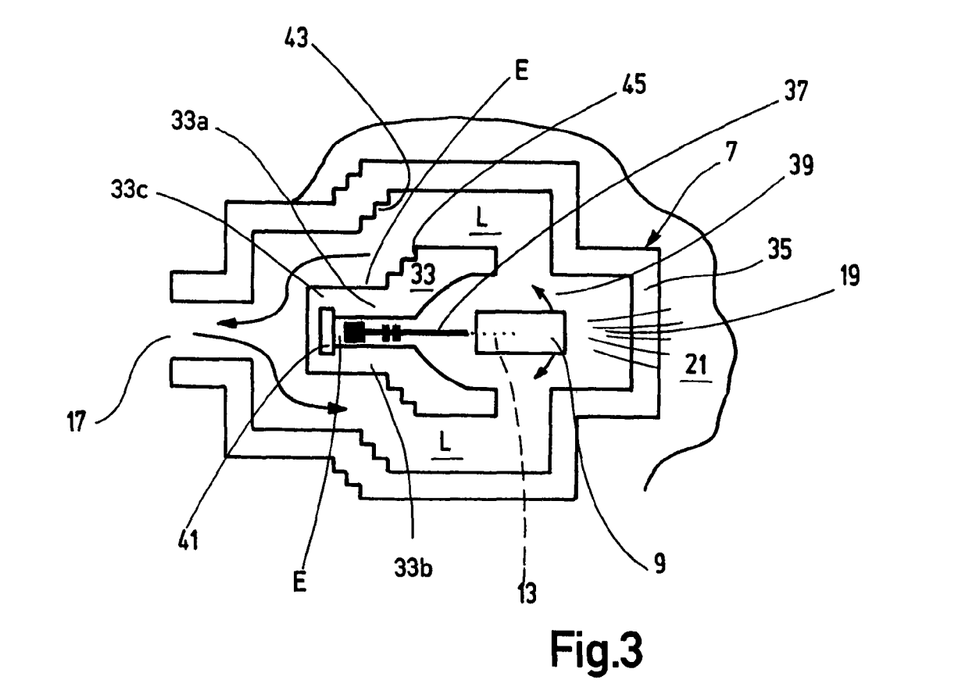
FIG. 3 a first embodiment of a therapy room in top view.

In larger scale, FIG. 3 shows a therapy room 7 being apparent from FIG. 2. Same parts are referred to by same referrals so that it is insofar referred to the preceding description.

The therapy room 7 is surrounded by a conventional shielding wall 35, for example by a concrete wall with a thickness of one meter. The thickness of the wall 35 may be fitted to the different use cases; as well the shielding material. So it is known for example from DE 103 12 271 A1 to use gypsum for shielding. Outside the therapy room 7, there is the soil 21.

With the illustration according to FIG. 3, the access 17 of the therapy room 7 is given on the left side. Inside this room, the entrance region E of the partial beam T depicted in the FIGS. 1 and 2 may be seen in a distance to the access 17. The partial beam is surrounded by a shielding 33 being practically located in the middle of the therapy room 7.

From the schematic diagram according to FIG. 3 it is, as already from FIG. 1, apparent that one may enter the therapy room 7 via the access 17 without being exposed to any hazard by the treatment beam 13. Therefore, one may reach the shielding 33 from a room 15, mentioned in FIG. 1, which room is arranged left to the access 17.

The treatment beam 13 exits the beam tube being apparently here with the usual deflecting and scanning components, which are here arranged in the therapy room 7. The treatment beam is directed onto the treatment site 9, at which a couch for the patient is provided. By the double-headed arrow 39 it is indicated that the couch may be rotatable.

The treatment beam 13 exits the beam tube 37 and the shielding 33, which is open towards the treatment site 9, and hits the treatment site 9. Neutron radiation 19 given beyond the treatment site 9 is directed away from the access 17 and enters the soil 21 through the wall 35.

With the embodiment depicted in FIG. 3, a labyrinth is provided each to the right and to the left of the shielding 33—seen in the direction of the treatment beam 13. Those labyrinths serve to absorb radiation reflected by the treatment site 9. Thereby, it is possible to implement the access 17 without a heavy shielding door, what facilitates and accelerates the accessibility to the treatment site 9.

With the embodiment depicted here, it is further provided that the shielding 33 comprises a shielding reinforcement 41 preferably made from iron in its region, which also points to the access 17, opposite to the treatment site 9.

The labyrinths L located to the right and to the left of the entrance region E and of the shielding 33 inside the therapy room 7 are here implemented by steps 43 and 45 provided at the inside of the wall 35 and at the out side of the shielding 33. But it is also imaginable here to provide wall sections projecting into the aisles of the labyrinths L.

From the top view according to FIG. 3, it is apparent that the therapy room 7 is constructed symmetrically, wherein also the shielding 33 surrounds the entrance region E symmetrically.

The shielding 33 provides two wall regions 33a and 33b located opposite to each other, between which the entrance region E is arranged. At the end of the shielding facing the access 17, the wall regions 33a and 33b are connected with each other by a base section 33c so that the essentially U-shaped form of the shielding 33 is implemented. On the side facing the base section 33c, the wall regions 33a and 33b diverge substantially funnel-shaped towards the treatment site 9. With other words: The region of the shielding 33 being between the wall regions dilate, seen downstream the entrance region E, towards the treatment site 9 so that a funnel-shaped absorbing region for neutron radiation reflected by the treatment site 9 results. Therefore, this radiation is optimally absorbed by the shielding 33 so that the radiation exposure is reduced to a minimum on the side of the shielding facing the treatment site 9, thus in the region of the access 17 and of rooms 15 following thereto.

With the embodiment depicted in FIG. 3, the shielding 33 is free-standing in the therapy room 7 so that on both sides, an aisle results between the wall 35 of the therapy room 7 and the outside of the shielding 33, namely the labyrinths L mentioned above. With this embodiment of the therapy room 7, it is provided that the limiting wall of the therapy room 7 facing away the access 17 and located to the right of the treatment site 9 has a region protruding into the soil 21 so that operating staff may easily compass the treatment site 9 or a couch respectively provided there for the patient provided. Concerning its dimensions, this protrusion is fittable to the space required.

Figure 4:
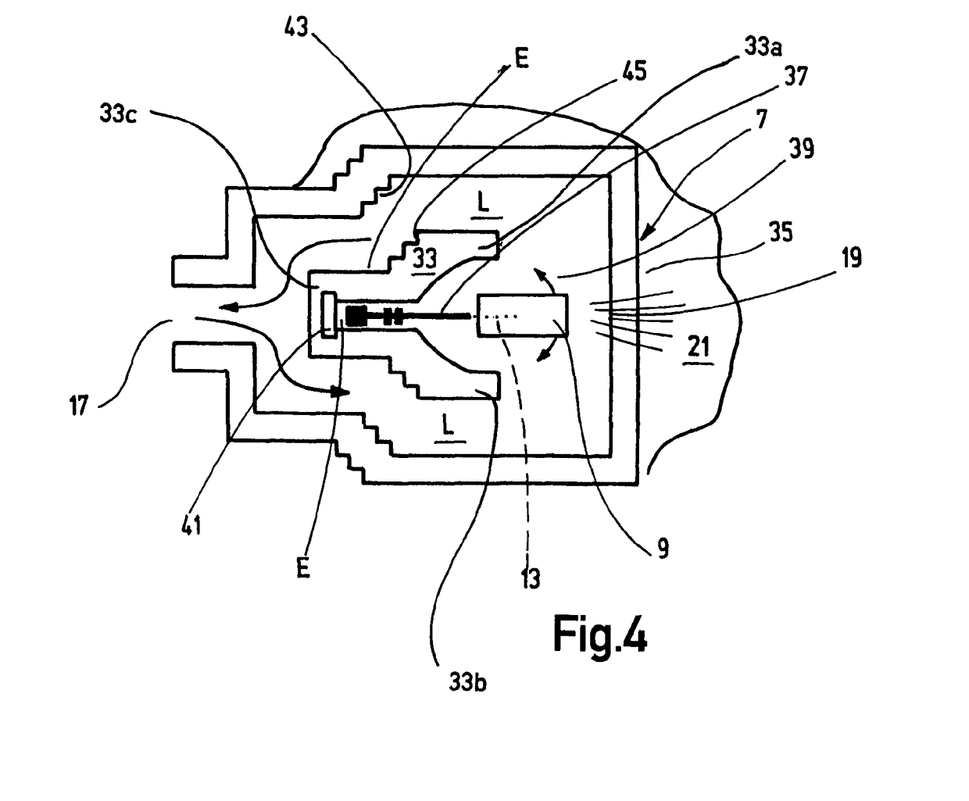
FIG. 4 a modified embodiment of a therapy room shown in FIG. 3 in top view.

FIG. 4 shows an embodiment of a therapy room 7, which is modified in comparison with the one depicted in FIG. 3. Same parts are referred to by same referrals so that it is insofar referred to the description of FIG. 3.

The therapy room 7 according to FIG. 4 is constructed a little bit easier than the one depicted in FIG. 3: The limiting wall of the therapy room 7 facing the access 17 may be arranged in a slightly larger distance to the shielding 33 than provided in FIG. 3 so that there is enough space to encompass a patient couch on the side facing the entrance site E. For that purpose, here the limiting wall of the therapy room is constructed straightly; thus the protrusion depicted in FIG. 3 is set aside, what reduces the manufacturing costs of the therapy room 7.

But here, the same basic principle is implemented, too: The mean neutron radiation cone, which is directed from the treatment site 9 to the right, is guided through the wall 35 of the therapy room 7 into the soil 21. Neutron radiation reflected by the treatment site 9 is absorbed by the shielding 33 and therefore reaches the access extremely attenuated, if at all.

Incidentally, the interior construction of the therapy room, particularly of the shielding 33, identical to the embodiment shown in FIG. 3 so that it is referred to the preceding comments to avoid repetitions.

Figure 5:
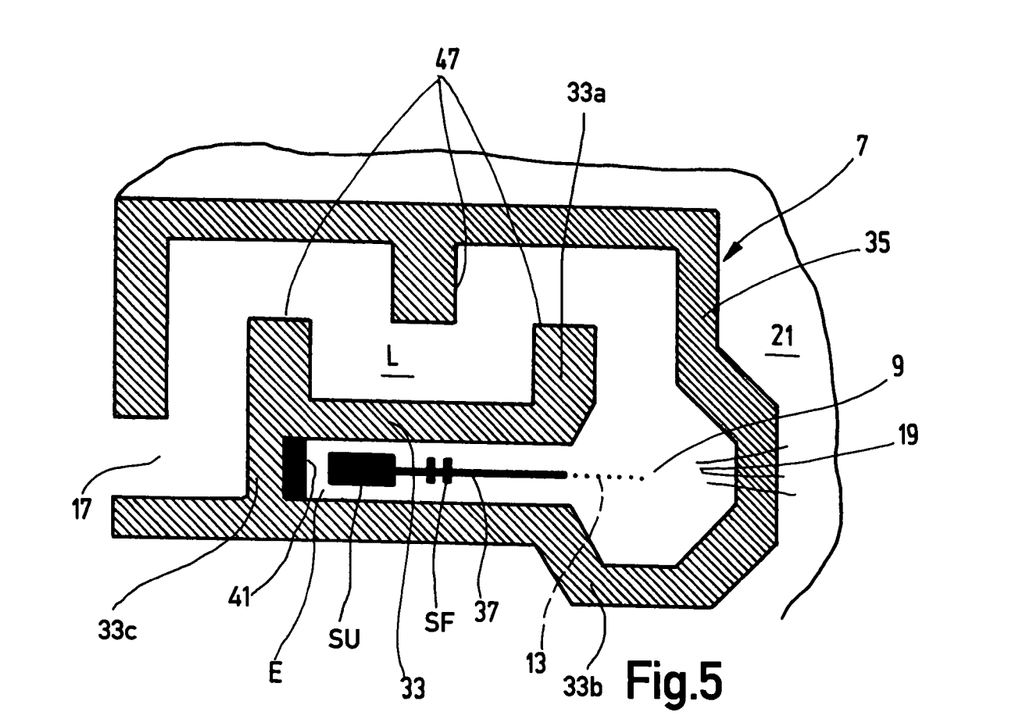
FIG. 5 a further embodiment of a therapy room in top view.

FIG. 5 shows a modified embodiment of a therapy room 7. Same parts are referred to by same referrals. Insofar, it is referred to the preceding comments to avoid repetitions.

It becomes apparent that the second embodiment is constructed asymmetrically. But the basic structure is identical:

The therapy room 7 is surrounded by a wall 35, which may consist of usual shielding concrete or the like. Outside the therapy room 7, there is soil 21. Left in FIG. 5, the access 17 to the therapy room 7 can be seen. In a distance to this, there is the entrance region E, in which a partial beam T, as explained in the FIGS. 1 to 3, enters the interior of the therapy room 7 through the floor of the therapy room 7 and is there deflected as well as formed. Since in the region of the access 17, the partial beam T proceeds below the floor of the therapy room 7 or above the ceiling, the region between the access 17 and the shielding 33 is not disturbed and accessible without danger.

The treatment beam 13 is guided by an usual beam tube 37 towards the treatment site 9, wherein the treatment beam 13 exits to the right, as seen from the beam tube 37, so that the access 17 is not exposed in any way. Neutron radiation generated in the region of the treatment site 9 is directed to the right and enters the soil 21 through the wall 35, so that here a specially powerful shielding made from concrete or the like can be omitted here.

The entrance region E is surrounded by a shielding 33 being open towards the treatment site 9, wherein in FIG. 4 above the shielding a labyrinth L is made, which has wall section 47 protruding into the aisle of the labyrinth. But it is imaginable here to provide steps, as explained by means of FIG. 3.

The therapy room 7 is constructed very compactly, because a labyrinth located below the shielding 33 is omitted and a part of the shielding is formed by a region of the wall 35.

Therefore, concerning its basic design, the shielding 33 is identical to the one described by means of FIG. 3: it has an upper wall region 33a and a facing lower wall region 33b. The entrance region E is located between these wall sections. Here, the beam deflecting device SU and the beam forming device SF are arranged, too. The two wall regions 33a and 33b are connected with each other by a base section 33c, so that again the U-shaped shielding 33 is formed as described above. Also here, a shielding reinforcement 41 is provided in the region of the base section 33c, as it was described above.

Therefore, the shielding 33 is closed towards the access 17 and open towards the treatment site 9. Also here, it is provided that the wall regions 33a and 33b dilate towards the treatment site 9 on the side facing away the base section 33c, so that a region absorbing reflected neutron radiation is formed, as it is also given with the embodiments according to the FIGS. 3 and 4.

In comparison with the embodiments according to the FIGS. 3 and 4, a difference has to be seen in the fact that a wall section of the shielding 33, here the lower wall region 33b, is part of the wall 35 surrounding the therapy room 7, while the opposite wall region 33a is free-standing in the therapy room 7.

With the embodiment depicted in FIG. 5 also, as may be seen from the embodiments depicted in the FIGS. 1 to 4, the therapy room 7 is freely accessible via the access 17. No special shielding door is needed here. The treatment beam 13 reaches the therapy room 7 via the entrance region E, is there deflected and formed and exits via the beam tube 37 and therefore reaches the treatment site 9. Thereby, the beam direction is away from the access 17. Neutron radiation 19 generated at the treatment site 9 is also directed away from the access 17, thereby also away from regions located in the left of the access 17. Radiation reflected by the treatment site 9 is optimally shielded against the access 17 by the shielding 33, particularly, also due to its funnel-shaped dilation towards the treatment site 9.

It is common to all embodiments that a limited part of the therapy room 7 from the entrance region E to the treatment site 9 and a region located downstream of the treatment site, exposed to neutron radiation 19 is shielded against radiation very well. The shielding 33 being used for this purpose surrounds the entrance region E on both sides, furthermore the beam deflecting device SU and the beam forming device SF. Moreover, the shielding device 33 protects against reflected neutron radiation, so that the remaining regions of the therapy room are exposed to a very highly reduced radiation level. By the fact that the treatment beam 13 reaches the therapy room from above or from below in the entrance region E, on the side of the shielding facing the treatment site 9, there are free regions, namely the access 17, via which the therapy room can be entered unhindered.

Therefore, the therapy room 7 may optimally be used, because no disturbing structural elements are present from the access 17 till the shielding 33. Incidentally, it is ensured that the treatment beam 13 is, as seen from the access 17, directed away towards the treatment site 9. The shielding 33 is located on an imaginary connecting line between the access 17 and the treatment site 9, wherein just the treatment beam 13 and therewith neutron radiation emanating from the treatment site 9 is directed away from the access. Therefore, no further special shielding measures are needed in the region of the access 17 and of rooms following there to the left. Radiation generated in the entrance region E and neutron radiation reflected by the treatment site 9 are optimally absorbed by the shielding 33.

Therefore, also with the embodiment depicted in FIG. 5, the treatment beam 13 does not enter the therapy room 7 through a side wall but through the floor. In principle, a leading-in through the ceiling would be possible, too. Beam guiding devices as described by means of the FIGS. 1 and 2 are therefore arranged below or above of the therapy room 7 and do therefore not disturb the access 17, which is hit neither by the treatment beam 13 nor by the neutron radiation 19. Scattered radiation being generated in the region of the treatment site 9 is caught by the shielding 33 and by the labyrinth L so effectively that heavy shielding doors can be omitted in the region of the access 17.

Figure 6:
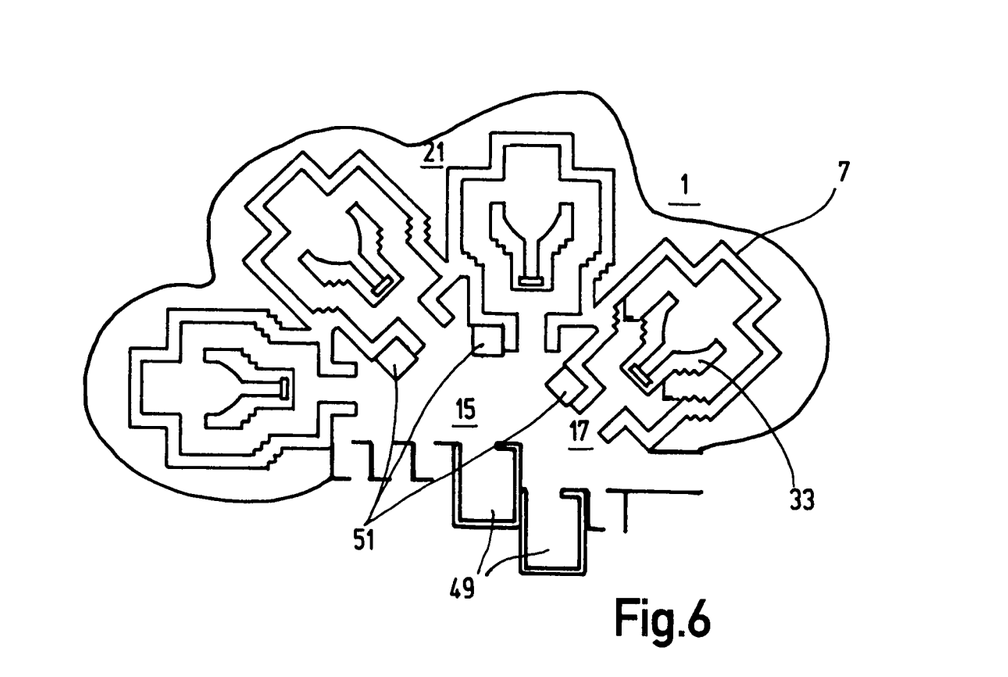
FIG. 6 a number of therapy rooms according to FIG. 3 in curved arrangement.

By means of the FIGS. 6 to 9, different alternatives for arranging the therapy rooms shall be discussed:

FIG. 6 shows a number of symmetrically arranged therapy rooms 7, as they were already discussed in the FIGS. 2, 3, and 4. Preferably, they are formed identically and have labyrinths L arranged symmetrically to the middle axis of the therapy room 7. The labyrinths form a connection between the access 17 and the treatment site 9, and are routed past in the right and in the left of the shielding 33.

In all cases, depicting the beam tube 37 was omitted, because in this context the arrangement of the therapy rooms is important only. They are placed as close as possible, so that touch points and common wall regions result quasi. The accesses of all therapy rooms 7 lead to a room 15, which serves for preparing and medically caring patients, and may comprise X-ray regions 49 and bedding rooms for patients as well as central control rooms for assistant medical technicians, who operate and monitor the irradiation device 1, particularly the devices assigned to the several therapy rooms 7. The X-ray regions 49 particularly serve to verify the positions of the patients. In this context, it is explicitly pointed out that X-ray diagnostics for verifying the position may be carried out in the therapy rooms 7, too.

According to FIG. 6, the therapy rooms 7 are arranged in a curved manner, in order to be able to use the common space 15 optimally, and to limit the total space-required for the therapy rooms 7 to a minimum. Also here, the therapy rooms 7 are, as indicated by a line, surrounded by soil 21, so that neutron radiation 19 given downstream of the treatment site 9 is absorbed by the soil 21, and expensive shieldings for that purpose can be omitted.

Figure 7:
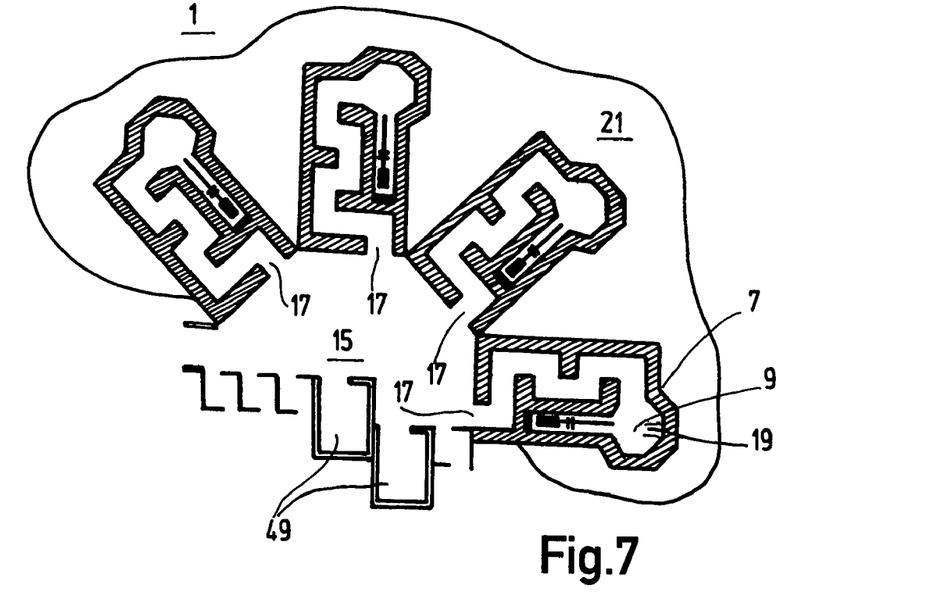
FIG. 7 a number of therapy rooms according to FIG. 4 in curved arrangement.

FIG. 7 shows another embodiment of an arrangement of therapy rooms 7. Here, therapy rooms, as they were described by means of FIG. 5, are arranged in a curved manner. Therefore, here, in contrast to FIG. 6, asymmetrical therapy rooms are arranged in a curved manner, wherein their accesses lead to a common room 15, in which patients may be subject to precaution and aftercare and may lie. Furthermore, X-ray regions 49 may be provided here as well as central control rooms not depicted here in detail for operating the irradiation device 1 and for carrying out the treatment of patients in the therapy rooms 7.

Also with the embodiment depicted here, as in FIGS. 2 and 6, the therapy rooms 7 are arranged in such a manner that the treatment beams 13 and the neutron radiation 19 are directed away outward and hit the soil 21 surrounding the therapy rooms 7. The room 15 is exposed neither to the treatment beam 13 of the several therapy rooms nor to the neutron radiation, which may be generated in the region of the treatment sites 9.

Figure 8:
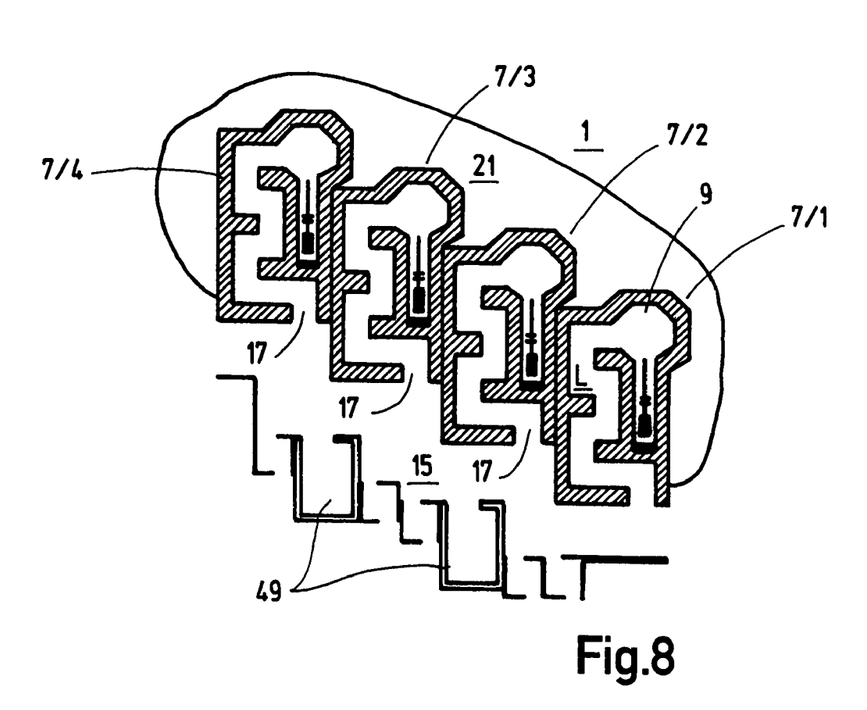
FIG. 8 a number of therapy rooms according to FIG. 4 in parallel arrangement and
FIG. 9 a number of therapy rooms according to FIG. 4 in mirrored arrangement.

Finally, FIG. 8 shows an irradiation device 1 with a number of therapy rooms 7, as they were discussed by means of FIG. 5. Therefore, here it is a matter of asymmetrical therapy rooms 7 with one labyrinth only.

As from FIG. 5, it is apparent from the illustration according to FIG. 8 that quasi a bulge is given in the region of the treatment site 9, but that incidentally the therapy rooms 7 have side walls proceeding in parallel to each other. With the illustration according to FIG. 8, the therapy rooms 7 are arranged in parallel to each other and are offset in longitudinal direction to each other, so that the parallel wall regions of two adjacent therapy rooms rest with each other, and therefore a minimal space-required is given.

Also here, the accesses 17 of the therapy rooms 7 lead to a room 15, which may comprise X-ray regions 49 or central control rooms not depicted here in detail.

Also here, the arrangement and the alignment of the therapy rooms 7 are chosen in such a manner that the treatment beams 13 and the neutron radiation 19 are directed away from the access 17 and the room 15 and are shielded by the soil 21 surrounding the therapy rooms.

Since the treatment beams 13 and the neutron radiation 19 do not expose the access 17 here, too, shielding doors can be omitted, so that an easy and quick access to the treatment sites 9 is possible. But with the asymmetrical therapy rooms 7, one has to assume that the labyrinth L may only be used alternatively as entrance or as exit, respectively.

Figure 9:
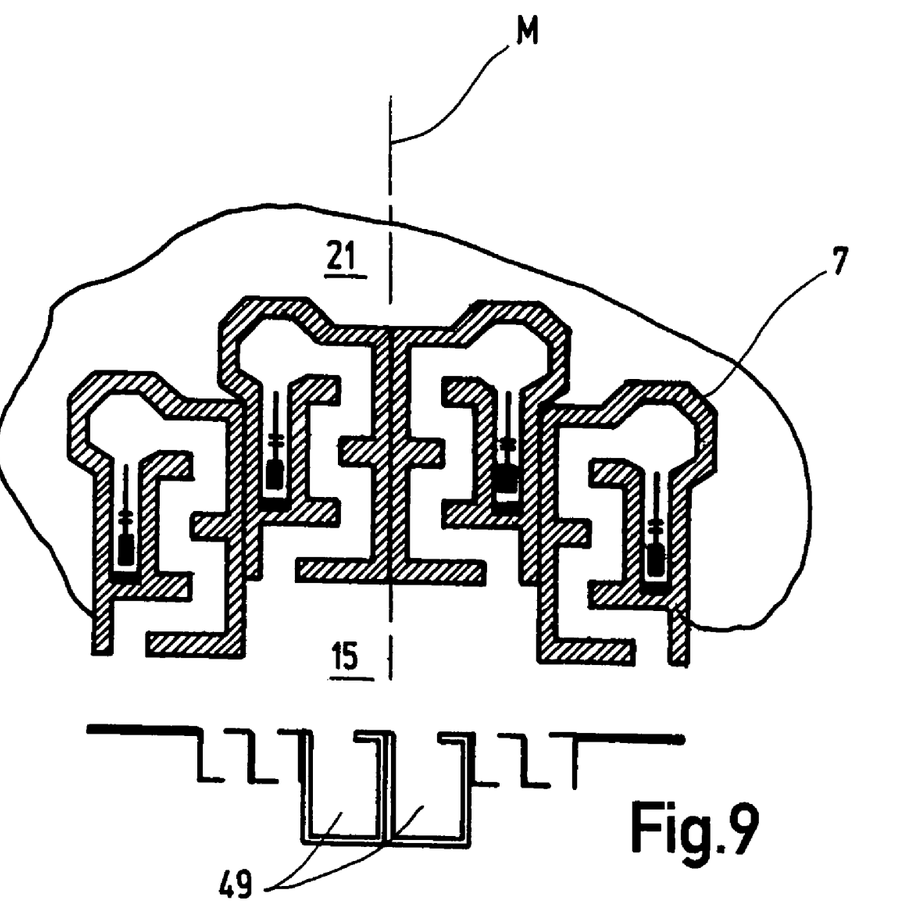

Finally, in FIG. 9 yet an embodiment is depicted, with which four therapy rooms 7 of an irradiation device 1 are illustrated. These are arranged in a mirrored manner with respect to an indicated middle plane M, wherein also the therapy rooms are formed in a mirrored manner to the right and to the left of the middle plane M: In case of the therapy rooms located to the right of the middle plane M, the labyrinth is in the left of the shielding 33 of the entrance region E, in case of the therapy rooms located in the left of the middle plane, in the right thereof. The accesses 17 of the therapy rooms again lead to a common room 15, in which patients may be pre-treated and after-treated. Here, X-ray regions may be seen, too. Also here, central control rooms may be provided, which, however, are not depicted.

Also here, the therapy rooms 7 are arranged in a space-saving, close-packed manner, wherein it is ensured in each case that the treatment beams 13 and the neutron radiation 19 do not hit the accesses 17 and the common room 15. In each case, the neutron radiation 19 is rather directed outwards, and is absorbed by the soil 21 surrounding the therapy rooms 7.

In total, it is apparent that the irradiation device 1 may provide different therapy rooms 7, which may be arranged to each other in different ways. When doing so, symmetrically constructed therapy rooms with two labyrinths and asymmetrically constructed therapy rooms with one labyrinth each may be employed. As necessary, it is very well possible to combine symmetrical and asymmetrical therapy rooms in order to ensure an optimal space utilization. In any case it is guaranteed that at least the therapy rooms 7 and the beam guiding devices 5 are arranged on different planes, so that the accesses 17 to the therapy rooms 7 may be arranged optimally. The beams each are leaded into the interior of a therapy room in a distance to the limiting walls thereof, so that inside the therapy rooms 7 in each case, an entrance region E may be surrounded by an own shielding, and the access 17 is protected against the treatment beam 13 and the neutron radiation 19.

In total, it is apparent that the irradiation device 1 is constructed very compactly and that the distribution of therapy room 7, radiation source 3 and/or beam guiding device 5 on different planes quasi allows nesting the elements of the irradiation device 1, what results in a very compact design. Moreover, the therapy rooms are constructed in such a manner that the beam might not be guided through a side wall of the therapy room 7, but through the ceiling thereof into the interior and may be directed to the treatment site 9. By doing so, it is possible to position the access 17 in such a manner that it is exposed neither by the treatment beam 13 nor by the neutron radiation 19, and that a labyrinth may be formed between the access 17 and the treatment site 9. The labyrinth may be formed symmetrically to the entrance region E of the beam into the therapy room 7, and has an entrance and an exit. The therapy rooms will become yet more compact, if only one single labyrinth is provided, which serves as entrance as well as exit.

The irradiation device 1 may be positioned closely to a treatment or research centre as well as to a hospital 23, because the treatment beams 13 and particularly the neutron radiation 19 is directed away from the access 17 and away from the rooms 15 preceding the access 17. When doing so, expensive shielding measures are omitted, because the treatment beam 13 and the neutron radiation 19 penetrate the soil 21 surrounding the therapy room 7, and are caught by it.

Therapy rooms constructed in such a manner may be arranged closely to each other in a curved manner or in parallel to each other, wherein an offset stringing together of therapy rooms 7 is possible, too. By doing so, a common room 15 may also be associated with several therapy rooms 7, what further optimizes the space use.

Particularly from the FIGS. 8 and 9, it becomes apparent that with the arrangement of therapy rooms shown here, wall sections may be formed thinner or may be omitted totally, in order to save shielding material and space. Particularly, this applies in regions, in which wall sections of adjacent therapy rooms are adjoin. Here, in case of usual devices, often a wall thickness results, which exceeds the thickness being desired for shielding purposes.

What is claimed is:

1. An irradiation device for proton or ion beam therapy comprising:
    a radiation source (3) that comprises a cyclotron or synchrotron arranged horizontally in a first plane (E3) for generating a treatment beam;
    a beam guiding device (5) installed downstream of the cyclotron or synchrotron, wherein the beam guiding device guides the treatment beam from the cyclotron or synchrotron into a therapy room (7);
    wherein the therapy room (7) is arranged in a second plane (E1) located above the first plane (E3), and wherein the therapy room comprises a treatment site (9) and an access (17);
    wherein a floor (B) of the therapy room comprises an entrance region (E) that enables the treatment beam to enter the therapy room (7) in the second plane (E1), and wherein the entrance region (E) is arranged between the treatment site (9) and the access (17) in the second plane;
    wherein the therapy room comprises a shielding that surrounds, at least in part, the entrance region (E), and wherein the shielding is open towards the treatment site (9) in the second plane so that the access (17) is arranged on the open side of the shielding (33) that is facing away from the treatment site (9);
    wherein the beam guiding device (5) is configured to guide the treatment beam (13) from the first plane of the cyclotron or synchrotron into the second plane of the therapy room (7) via the entrance region (E), and wherein the treatment beam (13) is deflected between the access and the treatment site within the therapy room in such a way that the treatment beam is directed towards the treatment site (9) and in an opposite direction of the access (17); and
    wherein the therapy room comprises at least one labyrinth (L) positioned in the second plane, and wherein the labyrinth is laterally offset in relation to the treatment beam (13) proceeding in the therapy room (7) and laterally offset to the shielding (33).

2. The irradiation device according to claim 1, wherein said treatment beam (13) entering said therapy room (7) in said entrance region (E) is conducted to a beam deflecting device (SU) and/or to a beam forming device (SF), which is/are arranged in said therapy room (7).

3. The irradiation device according to claim 1, wherein said treatment beam (13) proceeds towards said entrance region (E) below or above said access (17).

4. The irradiation device according to claim 1, wherein said shielding (33) comprises two wall regions (33a, 33b), between which said entrance region (E) is located, one of which said wall regions (33a, 33b) may be part of a shielding wall (35) of said therapy room (7).

5. The irradiation device according to claim 2, wherein said beam deflecting device (SU) and/or said beam forming device (SF) is/are arranged between wall regions (33a, 33b) of said shielding (33).

6. The irradiation device according to claim 5, wherein said shielding (33) has a base section (33c) connecting wall regions (33a, 33b).

7. The irradiation device according to claim 6, wherein said base section (33c) has a shielding reinforcement (41).

8. The irradiation device according to claim 7, wherein said wall regions (33a, 33b) of said shielding (33) dilate towards said treatment site as seen downstream from said entrance region (E).

9. The irradiation device according to claim 1, wherein said shielding (33) is symmetrically constructed.

10. The irradiation device according to claim 1, wherein the labyrinth (L) is provided between said access (17) and said treatment site (9) on both sides of said shielding (33).

11. The irradiation device according to claim 1, wherein at least one room (15) is arranged on said second plane for pre-treatment and after-treatment of patients treated at said treatment site (9) and for the stay of other persons.

12. The irradiation device according to claim 11, wherein said treatment beam (13) directed out of said entrance region (E) towards said treatment site (9) is directed away from said at least one room (15).

13. The irradiation device according to claim 1, wherein said treatment beam (13) is directed in an angle onto said treatment site (9).

14. The irradiation device according to claim 1, wherein said treatment beam (13) proceeds in parallel to the floor (B) of said therapy room (7).

15. The irradiation device according to claim 1, wherein said beam guiding device (5) is arranged in a third plane (E2).

16. The irradiation device according to claim 1, wherein said therapy room is one of multiple therapy rooms (7/1, 7/2, 7/3, 7/4) that are arranged in a curved manner to each other.

17. The irradiation device according to claim 1, wherein said therapy room is one of multiple therapy rooms (7) that are arranged in parallel to each other.

18. The irradiation device according to claim 17, wherein said multiple therapy rooms are arranged offset to each other.

19. The irradiation device according to claim 1, wherein said therapy room is one of multiple therapy rooms that are mirrored arranged and/or formed.

20. An irradiation device comprising:
    a radiation source,
    a beam guiding device, and
    a therapy room into which a treatment beam is directed, said therapy room comprising a treatment site and an access, characterized in that said therapy room is arranged in a first plane;

a shielding is provided in said therapy room, said shielding being open towards said treatment site and associated with an entrance region of said treatment beam into said therapy room;

said beam guiding device is configured to direct said treatment beam from a second plane located above or below said first plane into said therapy room, within which said treatment beam is deflected and directed towards said treatment site so that said treatment beam is directed away from said access; and said access is arranged on that side of said shielding which is facing away from said treatment site, wherein a line that is coincident with said treatment beam as directed towards said treatment site passes through said access.

* * * * *

UNITED STATES PATENT AND TRADEMARK OFFICE
CERTIFICATE OF CORRECTION

PATENT NO. : 8,384,054 B2  Page 1 of 1
APPLICATION NO. : 11/996498
DATED : February 26, 2013
INVENTOR(S) : Fehrenbacher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this

First Day of September, 2015

Michelle K. Lee
*Director of the United States Patent and Trademark Office*